(12) United States Patent
Holländer et al.

(10) Patent No.: US 10,011,826 B2
(45) Date of Patent: Jul. 3, 2018

(54) PARALLEL EXTRACTION OF DIFFERENT BIOMOLECULES FROM FORMALIN-FIXED TISSUE

(75) Inventors: Vera Holländer, Unna (DE); Peter Porschewski, Langenfeld (DE)

(73) Assignee: QIAGEN GmbH, Hilden (DE)

( * ) Notice: Subject to any disclaimer, the term of this patent is extended or adjusted under 35 U.S.C. 154(b) by 1353 days.

(21) Appl. No.: 13/132,588

(22) PCT Filed: Dec. 4, 2009

(86) PCT No.: PCT/EP2009/066428
§ 371 (c)(1),
(2), (4) Date: Jun. 2, 2011

(87) PCT Pub. No.: WO2010/063837
PCT Pub. Date: Jun. 10, 2010

(65) Prior Publication Data
US 2011/0244468 A1     Oct. 6, 2011

(30) Foreign Application Priority Data
Dec. 5, 2008 (EP) .................................. 08021134

(51) Int. Cl.
*C12N 15/10* (2006.01)
*C07H 21/00* (2006.01)
*G01N 33/53* (2006.01)
*G01N 33/68* (2006.01)

(52) U.S. Cl.
CPC ..... *C12N 15/1003* (2013.01); *G01N 33/5308* (2013.01); *G01N 33/68* (2013.01)

(58) Field of Classification Search
CPC .................................................. C12N 15/1003
USPC ....................................................... 536/25.41
See application file for complete search history.

(56) References Cited

U.S. PATENT DOCUMENTS

| 2002/0045582 | A1* | 4/2002 | Margolin et al. ............... 514/21 |
| 2003/0229394 | A1* | 12/2003 | Ogle et al. ................... 623/2.14 |
| 2007/0160999 | A1* | 7/2007 | Calabrese .......... C12N 15/1003 435/6.11 |
| 2009/0124510 | A1 | 5/2009 | Porschewski et al. ............ 506/9 |
| 2009/0202998 | A1 | 8/2009 | Schlumpberger et al. ....... 435/6 |

FOREIGN PATENT DOCUMENTS

| DE | 10 2005 023 011 | 11/2006 |
| DE | 10 2005 060 738 | 6/2007 |
| WO | 01/46402 | 6/2001 |
| WO | 2004/080578 A1 | 9/2004 |
| WO | 2004/080579 | 9/2004 |
| WO | 2005/012523 A1 | 2/2005 |
| WO | 2005/054466 A2 | 6/2005 |
| WO | 2005/075642 | 8/2005 |
| WO | 2006/122898 A1 | 11/2006 |
| WO | 2006/127860 A2 | 11/2006 |
| WO | 2007/068794 A1 | 6/2007 |
| WO | 2008/021419 A2 | 2/2008 |

OTHER PUBLICATIONS

Becker et al., "Quantitative protein analysis from formalin-fixed tissues: implications for translational clinical research and nanoscale molecular diagnosis," *J. Pathol.* 211:370-378, 2007.
Nesatyy et al., "Recovery of intact proteins from silver stained gels," *Analyst* 127:1180-1187, 2002.
Qiagen, "Material Safety Data Sheet: acc. To ISO/DIS 1104," pp. 1-5, 2008, URL: http://www1.QIAGEN.com/Support/MSDS/US/Extraction_Buffer_EXB_US2.pdf [retrieved on Feb. 11, 2009].
Qiagen, "Qproteome FFPE Tissue Handbook: for the isolation of full-length proteins from formalin-fixed, paraffin-embedded tissues," pp. 1-19, 2006, URL: http://www1.QIAGEN.com/HB/QPROTEOMEFFPETISSUEKIT_EN.
Yamashita, "Heat-induced antigen retrieval: Mechanisms and application to histochemistry," *Progress in Histochemistry and Cytochemistry* 41:141-200, 2007.

* cited by examiner

*Primary Examiner* — Jezia Riley
(74) *Attorney, Agent, or Firm* — Seed IP Law Group LLP

(57) ABSTRACT

The present invention relates to a method of isolating/extracting in parallel various biomolecules, in particular nucleic acids and proteins, from the same fixed biological samples, to the quantification and analysis of the biomolecules isolated by the method of the invention, and to a kit for isolating/extracting in parallel various biomolecules from a fixed sample, to the use of said kit for diagnosing, prognosing, deciding the therapy of and monitoring the therapy of a disease.

7 Claims, No Drawings

PARALLEL EXTRACTION OF DIFFERENT BIOMOLECULES FROM FORMALIN-FIXED TISSUE

The present invention relates to a method of isolating/extracting in parallel various biomolecules, in particular nucleic acids and proteins, from the same fixed biological samples. The present invention also comprises quantifying and analyzing the biomolecules isolated by the method of the invention, a kit for isolating/extracting in parallel various biomolecules from a fixed sample, and using said kit for diagnosing, prognosing, deciding the therapy of and monitoring the therapy of a disease.

Fixing tissues in formalin for subsequent histopathological tests is standard practice these days, for example in order to distinguish healthy from diseased tissue. Formalin-fixed, paraffin-embedded (FFPE) tissue has been collected for decades and is the source of countless diagnostic studies. Said tissue is that of most organs, of various stages of a disease, prior to/after/during a therapy, and many more. FFPE tissue has the advantage of a very well preserved morphology. However, fixing tissues with formalin results in strong crosslinking of macromolecules in the cell, and therefore it has not been possible in previous approaches to achieve parallel extraction of nucleic acids and proteins from a singular sample of human or animal tissues, which is very much desired in hospitals or research, by this fixing method which has been tried and tested for decades.

Isolating various biomolecules, for example proteins and nucleic acids, in parallel from a single sample is particularly desirable, since firstly only a very small amount of sample material is usually available which is not sufficient for multiple separate purifications. Secondly, the sample material is composed heterogeneously, for example some tumor cells are present within a sandwich of healthy cells. In this case, separating or dividing the sample is not desirable because dividing the sample cannot guarantee that each subsample comprises the same amount of cells of the same kind. Only isolating the biomolecules such as DNA, RNA and proteins, for example, in parallel from an undivided sample ensures that all biomolecules to be investigated (analytes) originate from a comparable sample and can thus be related to one another.

Isolating nucleic acid molecules from FFPE tissues is standard practice these days and has been described comprehensively in the literature. Examples of such methods can be found in the international patent applications WO 2004/080578, WO 2005/012523, WO 2005/054466 and WO 2008/021419, with said methods having in common that preference is given to employing a protease for purifying the nucleic acids in order to destroy at the same time proteins that are present, such as nucleic acid-degrading enzymes for example. A simultaneous/parallel purification or isolation of proteins from the same sample is of course not possible with those approaches.

WO 2006/127860 describes the proteolytic preparation of peptide fragments from FFPE tissues by targeted proteolysis of the proteins present in said tissues. This involves treating two samples of tissue with different buffers at the same time to generate a peptide pattern from said samples. Simultaneous/parallel isolation of proteins and nucleic acids from the same sample is not mentioned.

WO 2006/122898 demonstrates that extracting proteins from fixed tissue can be improved substantially if the sample studied is first boiled in a detergent-containing buffer and then incubated further at a temperature above 60° C. Treating the samples in this way enables the isolated proteins to be quantified subsequently.

WO 2007/068764 describes a method in which a fixed tissue sample is contacted with a preferably aqueous solution containing a nucleophilic reagent, thereby enabling the crosslinking of the biomolecules due to formalin fixing to be dissolved more readily. The sample treated in this way may be used in further purification steps either for isolating proteins or for isolating nucleic acids. Said application does not describe a method of isolating in parallel/simultaneously both kinds of biomolecules from the same sample.

It was an object of the present invention to provide a method which enables various biomolecules to be captured from a single sample of a fixed tissue and, where appropriate, to be studied.

This object is achieved by a method of parallel purification of various kinds of biomolecules from the same biological starting material fixed by crosslinking, comprising
 a) a step of dissolving said crosslinking of the starting material,
 b) a step of separating the different biomolecules present in the starting material into at least one fraction (A) and at least one fraction (B), and
 c) isolating or detecting, or isolating and detecting different biomolecules from at least one of said fractions (A) and (B) of step b),
and a kit for performing said method. Preferred embodiments are included in the dependent claims.

Surprisingly, when performing known methods, in particular the method described in WO 2006/122898, (a) employing a protease-free buffer, (b) using a detergent, and (c) boiling the sample with subsequent incubation at above 60° C. for more than 50 seconds, it turned out that the formalin-caused crosslinking in the tissue results in sufficient dissolution of said crosslinking only in the case of proteins. Consequently, only proteins are isolated in a substantially quantitative manner in methods described to date, while the nucleic acids also present in the sample are not released or not released in relatively large amounts, but remain in the undissolved fraction of the sample. This led to the finding that these nucleic acids can be removed substantially by a simple mechanical removal step, for example by centrifugation or filtration, from the soluble protein fraction. Thus, according to the invention, the "protein status" and the "nucleic acid status" can be recorded separately from one another from the same starting sample. The nucleic acids may then be isolated from the undissolved, removed fraction by previously known nucleic acid isolation methods, for example: RNeasy FFPE and QIAamp FFPE (both from Qiagen, Hilden, Germany), which include protease treatment for further disruption of the undissolved fraction and a further heat incubation step. In this way, both kinds of biomolecules are prefractionated from one and the same sample in a single extraction step and then isolated separately from one another and thus made accessible to further (subsequent) analytical methods.

The term biomolecules comprises all biomolecules known to the skilled worker, for example natural or synthetic nucleic acids, for example nucleic acids introduced into the sample, linear, branched or circular, single- or double-stranded nucleic acids, RNA, in particular mRNA, siRNA, miRNA, snRNA, tRNA, hnRNA or ribozymes, genomic, plasmidic or organelle DNA, proteins, peptides and modified proteins, and also nucleic acids, proteins and peptides of infectious origin, antibodies, hormones, growth factors, lipids, oligosaccharides, polysaccharides, proteoglucanes, metabolites and drugs/medicaments, without being limited hereto.

A suitable biological sample is any biological sample suitable for fixing, such as, for example, cell-containing body fluids such as blood, sperm, cerebral spinal fluid, saliva, sputum or urine, leukocyte fractions, buffy coat, feces, swabs, puncture fluids, skin fragments, whole organisms or parts thereof, organs, organ fragments, tissues and tissue parts of multicellular organisms, preferably of insects and mammals, in particular of humans, for example in the form of sections, biopsies, fine needle aspirates or tissue sections, isolated cells, for example in the form of adherent or suspended cell cultures, plants, plant parts, plant tissues or plant cells, bacteria, viruses, yeasts and fungi, without being limited thereto. A particularly preferred starting material which may be used is a tissue section from human tissue.

The biological sample may be fixed with any fixatives known to the skilled worker, in particular with acids, alcohols, aldehydes, ketones or other organic substances such as in particular glutaraldehyde or formaldehyde, with particular preference being given to biological samples fixed with formaldehyde. According to a particularly preferred embodiment of the method of the invention, use is made of a biological sample fixed with formaldehyde and embedded in paraffin.

Formalin-fixed, paraffin-embedded (FFPE) tissues are routinely utilized worldwide for the histopathological diagnosis of diseased and healthy tissue because the morphology is very well preserved in FFPE tissues. However, macromolecules such as DNA, RNA and proteins usually cannot be studied any more adequately in tissue fixed in this way. Contrary to long-term experiences of scientists, a method of extracting intact proteins from FFPE tissue has recently been established: Becker et al. described an accurate determination of the expression content of proteins from clinical tissue samples (*J Pathol*. 211:370-8, 2007). This enabled clinical researchers to quantitatively analyze proteins on FFPE tissues, with comparison with available clinical data.

Methods of analyzing and/or detecting the nucleic acids and proteins isolated by the method of the invention may be any analytical methods known to the skilled worker, such as for example amplification techniques such as e.g. PCR, qPCR, RT-PCR, qRT-PCR, Whole Genome Amplification, gelelectrophoresis, blotting technologies such as Southern-blotting, Northern-blotting, and immunological methods such as Western-blotting, immunoprecipitation or affinity chromatography, microarray analyses, RFLP analyses (restriction fragment length polymorphism analysis), SAGE (serial analysis of gene expression), sequencing, SNP analyses, mutational analyses, epigenetic analyses such as, for example, analysis of methylation patterns, protein/antibody array, immunoprecipitation, high performance liquid chromatography (HPLC), fast protein liquid chromatography (FPLC), SELDI or SELDI-TOF, mass spectrometry, MALDI-TOF mass spectrometry, enzyme-linked immunosorbent assays (ELISAs), polyacrylamide gelelectrophoresis (PAGE), in particular 2-dimensional polyacrylamide gelelectrophoresis (2-D gelelectrophoresis), capillary electrophoresis, with enzymes also detection via their specific activity and more of this kind, without being limited thereto.

The present invention describes a method of isolating in parallel biomolecules, preferably proteins and nucleic acids, such as genomic (g)DNA or RNA, for example, from FFPE tissue and analysis thereof by means of sensitive and quantitative methods, it being possible to start from very small amounts of sample, for example from clinical biopsies.

Parallel isolation according to the present invention means that, starting from the same sample (i.e. from the identical starting material), various kinds of biomolecules, for example both nucleic acids and proteins, are purified in each case. To this end, for example, the protein fraction and the nucleic acid fraction are separated from one another, after a first step of dissolving the crosslinking due to formalin, and the biomolecules, preferably the biomolecules predominant in the particular fraction, are isolated from at least one of said fractions, preferably from each fraction. Preference is given to isolating the proteins from the soluble fraction and the nucleic acids from the insoluble fraction. Said further isolation after separation of the biomolecules from the fractions may be carried out at the same time or one after the other.

The isolation method of the invention enables both nucleic acids and proteins to be isolated from the same starting sample in a substantially quantitative manner and separately from one another. For example, said method also enables the structure, sequence and the methylation state of genes and/or expression of genes and to be compared with the protein status in the tissue.

The method described herein may be employed, for example, for recording diagnostically or therapeutically important markers in vivo in the context of the complex architecture and regulatory mechanisms of a tissue in question. To mention only one example of this kind of important marker, mention may be made by way of example of the epidermal growth factor receptor (EGFR) in respect of its protein expression and its DNA mutation profile in tumor tissue.

The present method may be employed both for clinical research and for studies focusing on the basic principles. Even more important is the fact that the method described herein of isolating biomolecules from formalin-fixed tissues can be incorporated in the best possible way into the daily clinical routine. This enables substantially more accurate diagnostic and therapeutic methods to be applied.

The invention described herein relates to a substantial optimization of extracting both proteins and nucleic acids from fixed biological samples such as tissue samples for subsequent analysis and in particular for quantifying said proteins and nucleic acids, which optimization is compatible with current high throughput methods, for example protein arrays and real-time PCR methods, both in clinical surroundings and in experimental research. For example, samples from various stages or courses of diseases are accessible in this way to analysis and quantification of the biomolecules present therein and therefore also allow retrospective analyses.

The present method enables intact proteins and nucleic acids from the same starting material to be detected and quantified. Proteins from completely different cell compartments such as, for example, the nucleus, the cytoplasm or the cell membrane can be reliably isolated and quantitatively determined. The isolated intact proteins can be diluted, i.e. serial dilutions and thus internal standard curves can be established. This may ensure that the detection and quantification of the proteins are within the linear range. If necessary, the proteins may be tested by means of Western blot beforehand, in order to ensure that there are no cross-reactions of the detection means used, for example antibodies (only one specific band of the right size in the Western blot). The intact proteins isolated and quantifiable in the manner described herein supplement in the best possible way results of immunohistochemical analyses such as those already carried out in the daily clinical routine. This enables intact proteins to be quantified accurately and sensitively and proteins to be cellularly assigned (immunohistochemistry) in the fixed tissue. At the same time, the protein status recorded may be compared with the expression pattern in the tissue or else with the quantity of individual expressed genes. Known disease markers, for example Her2/neu in breast cancer patients, may be clinically determined with high accuracy, at both expression level and translation level. In addition, novel disease markers may be identified by the method by way of comparison between a healthy and a diseased tissue by analyzing the expressed genes and/or the isolated intact proteins using common detection methods, for example mass spectrometry or quantitative PCR. Animal tissues may likewise be studied using the present method. Animal models are already available for many human diseases, for example cancers. The tissues to be studied are typically fixed in formalin, embedded in paraffin and then evaluated histopathologically. The present method may be employed for accurate, sensitive and powerful quantification, for example by means of protein arrays and quantitative PCR, of known and novel disease markers in said models.

According to the present method, the proteins present in the tissue are separated in a substantially quantitative manner from the nucleic acids present in said tissue in an early method step.

The term "in a substantially quantitative manner" means, according to the present invention, that two different fractions are obtained after the separation step, both of which contain biomolecules originally present in the tissue, with a fraction (A) containing more than 50% of total soluble proteins (i.e. of all proteins removable from the tissue) but less than 50% of all removable nucleic acids, while fewer than 50% of soluble proteins but more than 50% of nucleic acids remain in the other fraction (B) after the separation step. Preference is given to fraction (A) containing, after the separation step, more than 60%, further preferably more than 70%, particularly preferably even more than 75%, especially preferably at least 80%, of all proteins removable from the tissue, while fraction (B) contains more than 60%, further preferably more than 70%, particularly preferably more than 75%, especially preferably at least 80%, of all nucleic acids removable from the tissue, it being possible for said nucleic acids to still be bound in the insoluble components of the tissue after the first separation step.

According to the present invention, the term isolation is intended to mean the removal of the biomolecules concerned from other components of the starting material, without the need for a complete or substantial purification of said biomolecules. An isolated biomolecule thus means a biomolecule which is no longer in its original, natural environment, for example in a cell, but has been removed therefrom, and from which other cellular components have at least partially been removed. Thus, for example, separating soluble from insoluble components of a cell by disrupting said cell and subsequent centrifugation represents a step of isolating the soluble cellular components.

The term purification means that a biomolecule already separated from further cellular components (isolated biomolecule) is subjected to at least one further purification step in order to remove contaminations at least partially. For example, soluble proteins may be purified by chromatographic methods or else by dialysis of other soluble cellular components. In this context, purification is not supposed to mean that the purified biomolecule is afterwards without any kind of contamination. Rather the biomolecule is referred to as purified even upon an increase in the ratio of said biomolecule to other contaminations due to said purification step.

The term "removable" or "dissolvable" means that a biomolecule can be isolated by a suitable method. The term may be used both in respect of the kinds of biomolecules (e.g. proteins or nucleic acids) and of the amount of biomolecules that can be isolated from the starting material by suitable treatment. It should be noted here that a biomolecule may be referred to as removable even if it is still within an assemblage, i.e. has not been dissolved yet, but can be dissolved by a suitable method (for example also membrane proteins).

The individual steps of the method of the invention are described in more detail below:

The starting material used may be any material containing biomolecules, with preference being given to using a fixed starting material. Particular preference is given to using a tissue fixed with formalin, in particular an FFPE tissue. When an FFPE tissue is used, preference is given to deparaffinizing it first. The tissue areas to be studied may be removed either manually by way of microtome sections or tissue punches or by means of laser microdissection from the tissue section.

The deparaffinization which is preferably carried out first may distinctly influence the achievable yield of biomolecules. The deparaffinization generally serves to remove the paraffin used for embedding the biological sample. In general, said paraffin may cause trouble firstly when the biomolecules are dissolved and fractionated and secondly when the biomolecules are purified further and analyzed. Samples are usually deparaffinized by incubation in organic solvents such as xylene and/or ethanol, for example. In the process, the sample is normally first incubated one or more times in xylene, and said xylene is then removed by one or more incubations in 100% strength ethanol and, where appropriate, subsequently in diluted ethanol. Alternatively it is also possible to use other organic solvents for deparaffinization, such as, for example, alkanes, particularly preferably heptane, or other alcohols, for example methanol. A deparaffinization based on incubation in alkanes such as heptane, and addition of alcohol, particularly preferably methanol, has proved to be particularly advantageous in terms of high yields of high quality biomolecules by the described method.

Firstly, according to step a) of the method of the invention, the crosslinking present in the starting material, in particular the crosslinking of the biomolecules, is at least partially dissolved.

To this end, a suitable embodiment comprises (i) transferring the starting material, where appropriate after a deparaffinization step, to a preferably aqueous system which may advantageously contain a detergent and is free of proteolytically active compounds. For example, no proteases such as trypsin or proteinase K should be used in order to ensure that the proteins remain intact. For example, an aqueous solution or a buffer may be used which contains the substances described as advantageous hereinbelow.

The material present in the solution, for example in the buffer, is (ii) heated to a temperature which is sufficient to liberate the removable proteins present therein, with preference being given to boiling the material first (heating to from 95° C. to 100° C.). The incubation time may vary, for example from 5 minutes to 40 minutes. The boiling time to be set may depend, for example, on the size of the sample.

The samples are then (iii) incubated at a temperature above 60° C. (e.g. 80° C.). The incubation time at >60° C.

may vary, for example from 1 hours to 6 hours. The incubation time at more than 60° C. should preferably be at least 20 min, but preferably less than 16 hours. This results in a sufficient amount of intact proteins being dissolved which may then be either detected directly, analyzed and/or quantified, for example.

In a preferred embodiment of the method of the invention, the aqueous system employed in step (i) may be an aqueous solution, in particular a buffer.

A buffer suitable in accordance with the invention or a buffer system usually has a specific pH in the range from 1.0 to 12.0, preferably between pH 1.0 and 9.0.

The aqueous system may preferably include at least one reducing reagent, preferably dithiothreitol (DTT). We found that using a reductant, in particular using DDT, results in a particularly advantageous yield of isolated, intact protein. The particular advantage of this embodiment is that of the lysates obtained being able to be quantified particularly well directly by commercially available protein quantification assays known to the skilled worker, such as BioRad DC® or BCA-Assay® by Pierce, for example, and be employed in the further analyses. A dilution of the samples can be dispensed with. This avoids measurement inaccuracies and may ensure that equal amounts of protein are employed in the subsequent analyses (e.g. Western blot).

Furthermore, the buffer may additionally comprise reducing reagents such as 1,4-dithio-DL-threitol, dithioerythritol (DTE), tris(2-carboxyethyl)phosphine (TCEP) or monoethanolamine (MEA).

The reducing reagents are employed at a concentration in the range from 0.05 mM to 20 mM, preferably from 0.1 to 10 mM, further preferably from 0.5 to 5 mM, particularly preferably from 0.5 to 2 mM. The most suitable concentration within this range depends in individual cases on the reagent(s) employed, with 1 mM being a particularly suitable concentration of DTT.

Detergents for the method of the invention may be any detergents known to the skilled worker and suitable for cell lysis, more specifically the detergents used are anionic or nonionic detergents, preferably sulfate group-containing detergents, particularly preferably sodium dodecyl sulfate (SDS), sodium deoxycholate, 3-[N-(3-cholanamidopropyl)-dimethylammonio]-2-hydroxy-1-propane sulfonate (CHAPS), Triton X100, Nonidet P40 or Tween20.

The detergent concentration may be about 0.1-10%, for example. The concentration range is particularly preferably in the range of about 1-5%.

Moreover, the aqueous system may preferably include at least one nucleophilic reagent. A suitable nucleophilic reagent here is any Lewis base capable of transferring electrons to an empty orbital or to empty orbitals of a Lewis acid. Among said Lewis bases, particular preference is given to reagents which have at least one functional group that carries a negative charge, that is negatively polarized or that has at least one free electron pair.

Examples of compound comprising a functional group having a negative charge are alkali metal or earth alkaline metal alkoxides, alkali metal or earth alkaline metal hydroxides, alkali metal or earth alkaline metal halides, alkali metal or earth alkaline metal cyanides, and the like.

Reagents having at least one functional group which is negatively polarized are in particular those reagents that have at least one functional group containing two covalently linked atoms which differ in their electronic negativity according to Alfred and Rochow by at least 0.25, particularly preferably by at least 0.5, and additionally preferably by at least 1.0.

Nucleophilic reagents particularly preferred according to the invention, however, are those which have at least one functional group with one or two, particularly preferably with one, free electron pair(s), with most preference being given among these compounds again to those which have at least one primary, secondary or tertiary amino group of the structure I

in which $R^1$ is a $C_1$ to $C_{20}$ hydrocarbon group, preferably a $C_2$ to $C_{15}$ hydrocarbon group, and particularly preferably a $C_2$ to $C_{10}$ hydrocarbon group, a $C_1$ to $C_{20}$ hydrocarbon group having at least one heteroatom, preferably a $C_2$ to $C_{15}$ hydrocarbon group having at least one heteroatom, and particularly preferably a $C_2$ to $C_{10}$ hydrocarbon group having at least one heteroatom, or an optionally heteroatom-substituted aromatic ring system, $R^2$ is a $C_1$ to $C_{20}$ alkyl group, preferably a $C_1$ to $C_{10}$ alkyl group, and particularly preferably a $C_1$ to $C_2$ alkyl group, in particular a methyl group or an ethyl group, a $C_1$ to $C_{20}$ hydroxyalkyl group, preferably a $C_1$ to $C_{10}$ hydroxyalkyl group, and particularly preferably a $C_1$ to $C_2$ hydroxyalkyl group, or a hydrogen atom, with most preference being given to a hydrogen atom, and $R^3$ is a $C_1$ to $C_{20}$ alkyl group, preferably a $C_1$ to $C_{10}$ alkyl group and particularly preferably a $C_1$ to $C_2$ alkyl group, in particular a methyl group or an ethyl group, a $C_1$ to $C_{20}$ hydroxyalkyl group, preferably a $C_1$ to $C_{10}$ hydroxyalkyl group and particularly preferably a $C_1$ to $C_2$ hydroxyalkyl group or a hydrogen atom, with most preference being given to a hydrogen atom.

Nucleophilic reagents having a functional group of the structure I depicted above that are particularly preferred according to the invention are in particular those which have at least one functional group of the structure I in which at least one of the radicals $R^2$ and $R^3$, most preferably both radicals $R^2$ and $R^3$, is/are a hydrogen atom. In addition, preference is given in particular to those nucleophilic reagents which have at least one functional group of the structure I in which the nitrogen atom is covalently linked only to those atoms in the radicals $R^1$, $R^2$ and $R^3$ that are sp$^3$ hybridized. More specifically, none of the radical $R^1$, $R^2$ or $R^3$ should be able to delocalize the free electron pair on the nitrogen atom across the radicals $R^1$, $R^2$ and $R^3$, respectively. Preference is thus given in particular to none of said radicals $R^1$, $R^2$ and $R^3$ having, for example, the structure II

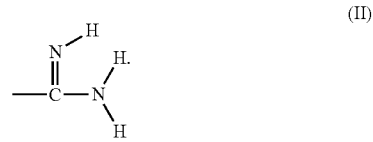

Nucleophilic reagents having at least one functional group of the structure I that are particularly preferred according to the invention are selected from the group consisting of methylamine, ethylamine, ethanolamine, n-propylamine, n-butylamine, iso-butylamine, tert-butylamine, dimethylamine, diethylamine, diethanolamine, di-n-propylamine, di-iso-propylamine, dibutylamine, trimethylamine, triethylamine, triethanolamine, hexamethylenetetramine, 2-ethylhexylamine, 2-amino-1,3-propanediol, hexylamine, cyclohexylamine, 1,2-di-methoxypropanamine, 1-aminopentane, 2-methyloxypropylamine, tri(hydroxymethyl)-aminomethane, aminocarboxylic acids, in particular glycine or histidine, or aminoguanidine, with most preference given among these to ethanolamine, diethanolamine, triethanolamine, amino-1,3-propanediol, aminoguanidine and tri (hydroxymethyl)aminomethane. Preferred nucleophilic reagents having at least one functional group of the structure I are furthermore aromatic amines selected from the group consisting of aniline, toluidine, naphthylamine, benzylamine, xylidene, xylenediamines, naphthalenediamines, toluenediamines, 3,3'-dimethyl-4,4'-diphenyldiamine, phenylenediamines, 2,4'-methylenedianiline, 4,4'-methylenedianiline, sulfonyldianiline, and dimethylbenzylamine.

According to one embodiment, in which the nucleophilic reagent has at least one primary amino group of the structure I, said nucleophilic reagent is a $C_1$ to $C_6$ alkylamine, a $C_1$ to $C_6$ alkyldiamine, a $C_1$ to $C_6$ alkyltriamine, a $C_1$ to $C_{15}$ aminoalcohol, a $C_1$ to $C_{15}$ aminodiole, or a $C_1$ to $C_{15}$ aminocarboxylic acid.

According to a further embodiment, the nucleophilic reagent is a heterocyclic compound including a nitrogen atom, selected from the group comprising pyrrole, pyridine, quinoline, indole, aza-cyclopentane, aza-cyclohexane, morpholine, piperidine, imidazole or a derivative of these compounds, with a derivative of these compounds preferably meaning a derivative in which a $C_1$ to $C_3$ alkyl group, particularly preferably a methyl group or ethyl group, rather than a hydrogen atom, is bound to one or more carbon atoms or to the nitrogen atom in the compounds listed above.

Among the nucleophilic reagents listed above, particular preference is given to those that are water-soluble, in particular those which have a solubility of at least 1 g/l, preferably at least 10 g/l, and particularly preferably at least 100 g/l, in water at a temperature of 25° C. and at pH 7.

The aqueous system comprising the above-described nucleophilic reagent may be based on pure, preferably deionized water or else on other, aqueous systems, in particular on mixtures of water and organic solvents such as alcohols, in particular mixtures of water and ethanol or methanol, the amount of water being preferably at least 50% by weight, particularly preferably at least 75% by weight, and most preferably at least 90% by weight, in each case based on the total weight of water and organic solvent, physiological salines, on buffers, in particular buffers including buffer components known to the skilled worker, such as, for example, TRIS, HEPES, PIPES, CAPS, CHES, AMP, AMPD or MOPS, in an amount in a range from 0.1 to 1000 mmol/l, particularly preferably 1 to 500 mmol/l, and most preferably 10 to 200 mmol/l, it being possible, where appropriate, for such a buffer component, depending on its structure, to be used also as nucleophilic reagent at the same time. It is furthermore also possible to employ nutrient media, such as MEM medium and DMEM medium, as an aqueous system. The aqueous solution containing the nucleophilic reagent is preferably prepared by simply mixing water or a corresponding aqueous system with the nucleophilic reagent.

The concentration of the nucleophilic reagent in the aqueous solution is preferably in a range from 0.1 to 10 000 mmol/l, particularly preferably from 1 to 5000 mmol/l, especially preferably from 5 to 2500 mmol/l, and most preferably from 20 to 1000 mmol/l. According to a particularly advantageous embodiment of the method of the invention, the concentration of the nucleophilic reagent in the aqueous solution is more than 20 mmol/l, particularly preferably more than 50 mmol/l, and most preferably more than 100 mmol/l.

Proteolytically active compounds in accordance with the invention are any protein-splitting compounds, for example proteolytically active enzymes such as proteases, in particular proteinase K, trypsin, chymotrypsin, papain, pepsin, pronase, and endoproteinase Lys-C. Proteolytically active compounds in accordance with the invention are moreover also non-enzymic substances suitable for splitting proteins, such as cyanogen bromide, for example.

According to step b) of the method of the invention, a step of separating the different biomolecules present in the starting material into at least one fraction (A) and at least one fraction (B) is carried out.

Preferably, said fractions are separated into at least one soluble fraction (A) and at least one insoluble fraction (B). Although it is also possible to divide the entire sample, including the soluble and insoluble components, into at least two fractions from which different biomolecules are then subsequently isolated or purified or in which different biomolecules can be detected or analyzed, preference is given to separating the sample after step (a) into at least one soluble fraction (A) and at least one insoluble fraction (B).

One advantage of these preferred embodiments of steps (a) and (b) of the method of the invention is the fact that the extracted/isolated, substantially intact proteins present in the soluble fraction (A) may be analyzed, quantified or specifically fractionated in step (c), even without a further purification step. More specifically, the extracted proteins may be fractionated using one or more method steps. However, it is of course also possible to purify the proteins present in fraction (A) over other soluble cellular components or to purify also individual proteins over other proteins present in fraction (A), before they are detected, analyzed or fractionated.

Fraction (B) which preferably contains insoluble components is subjected, preferably in a further step d) to further treatment for disrupting the undissolved sample components and, where appropriate, for dissolving the crosslinking of biomolecules. The removable nucleic acids which are substantially still in the insoluble fraction (B) can be isolated by this further treatment step.

Suitable for the treatment according to step d) is any known method for removing nucleic acids from fixed tissue, for example the methods as described in the international applications WO2007/068764, WO2008/021419, WO2005/012523 or WO2005/054466, or else the methods which may be carried out with the aid of commercially available kits, for example RNeasy FFPE® and QIAamp FFPE® (both from Qiagen, Hilden, Germany). With the latter, the insoluble components of fraction (B) are subjected to at least one further heat step and a treatment with a protease. Said protease treatment causes effective lysis and thus liberation of the removable nucleic acids.

The nucleic acids are isolated and optionally purified separately from the isolation and optionally purification of the proteins, it being possible for fractions (A) and (B) to be further processed at the same time but separately from one another, or one after the other.

The proteins may be purified/isolated by chromatographic methods, electrophoretic separation, specific binding to protein-binding materials, "protein capturing" with the aid of specific antibodies, or by precipitation.

The nucleic acids may be isolated and purified, after a further heat step and protease treatment of fraction (B), also by simple precipitation, by binding said nucleic acids to a nucleic acid-binding material, electrophoresis or chromatography, or by similar suitable methods familiar to the skilled worker. Preference is given to isolating and purifying said nucleic acids with the aid of a method as described in WO2007/068764 or WO2008/021419, or with the aid of the RNeasy FFPE® or QIAamp FFPE® kits (both from Qiagen, Hilden, Germany) according to the methods specified there.

Analysis is preferably carried out by any of the abovementioned analytical methods. Proteins are quantified preferably by means of the method according to Lowry or BCA, and other quantification methods, in particular protein arrays, may also be used for this. The nucleic acids are quantified by any suitable method, for example by quantitative PCR, by measuring the optical density of a defined dilution at 260/280 nm, or by comparative electrophoresis using predefined amounts of nucleic acids.

The extracted proteins may moreover be treated by means of proteolytic enzymes such as trypsin, chymotrypsin, proteinase K, papain, pepsin, pronase, endoproteinase LysC, endoproteinase Glu-C— or glycosidases—such as endoglycosidase H, Nglycosidase F, neuroaminidase), or phosphatases.

Advantageously, the proteins may be used for at least one biochemical assay. An example of a preferred biochemical assay is a protein array such as a microarray, in particular a sandwich immunoarray, antigen capture array or a direct protein array.

The biochemical assay may be used preferably for determining one or more diagnostically or clinically relevant marker proteins. This may involve, for example, comparing the marker proteins from at least two biological samples with one another. Thus it is possible, for example, to distinguish diseased from healthy. It is furthermore also possible to carry out the assay with a higher degree of multiplexing, in order to analyze at least one or more relevant markers.

The nucleic acids may be employed without limitation in any known analytical methods, in particular in the abovementioned methods.

The present invention likewise comprises providing a kit which may be used to isolate both intact proteins and nucleic acids from formalin-fixed human or animal biological samples such as tissues in a reliable manner and with high yield. Components of said kit are, for example, at least (1) a protease-free aqueous system for dissolving the crosslinking of the starting material, preferably a buffer system, (2) a detergent (this may optionally be present in solution (1)), and (3) a protease-containing solution, or a protease. Further components of the kit may be: (4) at least one nucleic acid-binding material, (5) further solutions or buffers for isolating nucleic acids, preferably a binding buffer and an elution buffer. A detailed protocol for isolating proteins and nucleic acids from formalin-fixed tissues may be enclosed with the kit.

The aqueous system (1) contained in the kit corresponds to the above-described aqueous system having all of the abovementioned possible components.

The example below is intended to describe the advantages arising from the present method. For example, the medicament Iressa® was shown to not significantly improve the rate of survival of patients suffering from non small cell lung cancer (NSCLC), the most common lung cancer variant. Overall, this EGFR inhibitor was effective only in every tenth patient. Indications of antitumorigenic efficacy was found with women, nonsmokers and patients of Asian descent. The reasons were that these patients carried genetic mutations in the EGFR gene resulting in sensitivity to Iressa®. In contrast, overexpression of the receptor played a minor part but was the decisive criterion during development of the new medicament. With a suitable assay, it would be possible to analyze both these mutations and the expression from the same sample without substantial losses and thus to establish which patient should respond to a treatment with Iressa®. Taking relatively large samples or taking two samples for in each case separate isolation of DNA and proteins could thus be avoided.

Since in the future there will be more and more targeted therapies and the corresponding diagnostics will have to be developed in parallel, parallel analysis of nucleic acids (in particular DNA, RNA) and proteins from extracts of FFPE tissues has a key role in predictive medicine. It is imperative here to quantify said molecules, i.e. to determine the level of expression or rate of translation or else both parameters of individual components, and to test the latter also for modifications with regard to the gene sequence (mutations, deletions).

EXAMPLES

Example 1

Separation of Biomolecules by the Method of the Invention

This experiment made use of formalin-fixed and paraffin-embedded tissue samples (FFPE samples) from rat liver. Sections of approx. 10 μm in thickness were prepared from said samples with the aid of a microtome, and two sections were used from each sample. Subsequent isolation of proteins and DNA/RNA from said FFPE sections used components of the RNeasy FFPE kit, the QIAamp FFPE kit, the Qproteome FFPE kit, and the Allprep DNA/RNA Mini kit from QIAGEN.

The tissues were first deparaffinized according to customary protocols. For example, the samples were first incubated in xylene for 10 min. After pelleting the sample and removing the supernatant, said xylene treatment was repeated twice. The samples were then treated in each case twice with 100% ethanol, with 96% ethanol, and 70% ethanol, as described above.

The deparaffinized sample pellets thus produced were admixed with 100 μl of EXB buffer from QIAGEN and boiled at 100° C. for 20 min to liberate the full length proteins. The samples were then incubated at 80° C. for another 2 hours. In this way, the proteins were liberated from the sample, and the crosslinking caused by formalin was dissolved. The nucleic acids were released into the solution not at all or only to a negligible degree by said inventive treatment of the samples and were able to be pelleted selectively by centrifugation, for example at 14 000×g for 15 min, while the proteins remained soluble in the supernatant which was separated from said pellet by removing it. Beside from the pelleted nucleic acids, completely insoluble components were also removed together with the nucleic acids, which components, however, did not influence further purification of DNA and RNA.

In order to find out about the presence of the various biomolecules, proteins and nucleic acids, in the two fractions, first, after centrifugation of the treated samples, the supernatant was removed and used separately from the pellet for further analyses and workups. Three samples were used for examining the distribution of the biomolecules in the fractions. From sample 1, the proteins were isolated from supernatant and pellet, from sample 2, DNA was isolated from supernatant and pellet, and sample 3 was used for isolating RNA from supernatant and pellet.

The supernatant of sample 1 was used without further processing for analyzing the proteins present therein.

To isolate DNA from the second sample, the supernatant was admixed with 200 µl of a chaotropic lysis buffer, for example buffer RBC from QIAGEN, and the mixture was applied to a silica membrane, for example in the Allprep DNA column from QIAGEN, and passed through the membrane by centrifugation at 10 000 rpm for 1 min. Addition of the chaotropic reagent produces conditions which enable the DNA, but not the RNA, to bind to the silica membrane. Said silica membrane was then washed by passing through 500 µl of the guanidine salt-containing wash buffer AW1 and subsequently 500 µl of the alcohol-containing wash buffer AW2, and 500 µl of 100% ethanol. The membrane was dried by centrifugation at 14 000 rpm for 5 minutes. The DNA was eluted by applying 30 µl of a DNA elution buffer, for example: ATE from QIAGEN, after one minute of incubation by centrifugation.

Similarly, RNA was isolated from the third sample by admixing the supernatant with 200 µl of a chaotropic lysis buffer, for example buffer RBC from QIAGEN, and applying said mixture to a silica membrane, for example in the Allprep DNA column from QIAGEN, and passing it through the membrane by centrifugation at 10 000 rpm for 1 min. Since the composition of said mixture results in DNA, but not RNA, binding to said silica membrane, said RNA is in the flow through of the column. To adjust the binding conditions for RNA, said flow through was mixed with ethanol and then again applied to a silica membrane, for example in the RNeasy MinElute column from QIAGEN, and passed through the membrane by centrifugation at 10 000 rpm for 1 min. The silica membrane was then washed by passing through 500 µl of the guanidine salt-containing wash buffer RW1, and subsequently 500 µl of the alcohol-containing wash buffer RW2. The membrane was dried by centrifugation at 14 000 rpm for 5 minutes. The RNA was eluted by applying 30 µl of water after one minute of incubation by centrifugation.

The pellet fractions of the three samples obtained by centrifugation of the sample treated according to the invention were also used for isolating proteins (sample 1), DNA (sample 2) and RNA (sample 3).

To isolate the proteins, the pellet of sample 1 was dissolved in a suitable protein lysis buffer such as, for example, the detergent-containing mammalian protein lysis buffer, and used for further analysis.

To isolate DNA, the pellet of sample 2 was admixed with a customary DNA lysis buffer such as, for example, 180 µl of the detergent-containing buffer ATL from QIAGEN. Since the pellet had only components which had not yet been dissolved by the prior treatment, additionally a lysis by means of a protease, for example 20 µl of proteinase K, was carried out in order to likewise dissolve said undissolved components. After incubation at 56° C. for 1 hour and subsequent incubation at 90° C. for 10 minutes, the lysate was admixed with a chaotrop-containing binding buffer, for example buffer AL from QIAGEN, and the mixture was applied to a silica membrane, for example in the QIAamp Mini column from QIAGEN, and passed through the membrane by centrifugation at 10 000 rpm for 1 min. The silica membrane was washed as described above by passing through wash buffers AW1, AW2 and 100% ethanol, the membrane was dried and the DNA was eluted.

To isolate RNA, the pellet of sample 3 was admixed with a customary RNA lysis buffer such as, for example, 150 µl of the detergent-containing buffer PKD and 10 µl of proteinase K from QIAGEN. After incubation at 56° C. for 1 hour and subsequent incubation at 80° C. for 15 minutes, the lysate was admixed with a chaotrop-containing binding buffer, for example buffer RBC from QIAGEN, and the mixture was applied to a silica membrane, for example in the RNeasy MinElute column from QIAGEN, and passed through the membrane by centrifugation at 10 000 rpm for 1 min. The silica membrane was washed as described above by passing through wash buffers RW1 and RW2, the membrane was dried and the RNA was eluted.

In order to determine the distribution of the proteins and nucleic acids isolated in this way from the two fractions, supernatant and pellet, the biomolecules of both fractions were quantified using suitable methods. The yield of the proteins present was determined by employing a BCA assay according to the manufacturer's information (Pierce). Yield and purity of DNA and RNA, respectively, were determined by measuring absorbents at 260/280 nm. The averages of the yields of multiple determinations are depicted in Table 1.

TABLE 1

| Analyte | Fraction | |
|---|---|---|
| | Supernatant yield/µg | Pellet yield/µg |
| Protein (sample 1) | 23.87 | 5.56 |
| RNA (sample 3) | 3.94 | 16.74 |
| DNA (sample 2) | 1.04 | 4.53 |

The results demonstrate that, using the method of the invention, the biomolecules are markedly fractionated prior to downstream purification. The proteins were absolutely predominantly in the supernatant, while the nucleic acids were located in the pellet fraction.

Example 2

Gel Analysis of the Biomolecules Fractionated by the Method of the Invention

DNA, RNA and proteins isolated from the pellet fractions and the supernatant fractions by the methods described in Example 1 were further analyzed by means of gel analyses.

Equal volumes of the proteins isolated from the two fractions were analyzed by customary methods by means of an SDS polyacrylamide gel which was subsequently stained with Coomassie. In this case, proteins were visible only in the supernatant fraction, while the pellet fractions did not have any visible proteins.

Equal volumes of the nucleic acids isolated from the two fractions were fractionated by customary methods on a TAE agarosegel and stained with ethidium bromide. The gels stained with ethidium bromide in all cases showed fragmented DNA or RNA in the fractions and in the controls, which can be identified by a bright "smear" distributed over a certain size range. The nucleic acids which can be isolated from FFPE samples were always fragmented because said nucleic acids had been degraded already during fixing, embedding and storing of the samples. It is also clearly visible that the pellet fraction had both distinctly more DNA and distinctly more RNA than the respective associated supernatant fraction.

Example 3

Real-Time RT-PCR Analysis of RNA Fractionated by the Method of the Invention In order to investigate the effect of the method of the invention not only on isolating the nucleic acids but also on analysis by means of amplification, the RNA which had been isolated from the pellet fraction and the supernatant fraction by the methods described in Example 1 was employed for further analysis by means of quantitative real-time RT-PCR.

The isolated RNA was used in each case in duplicate for detecting an amplicon of the madH7 transcript. The eluates were in each case diluted 1:5 with water, and 5 µl of said solutions were used in real-time PCR. Amplification was carried out in a total volume of 25 µl using a suitable mastermix for real-time RT-PCR, such as, for example, the QuantiTect SYBRGreen RT-PCR kit from QIAGEN, according to the manufacturer's information. Amplification was carried out in a suitable real-time amplification instrument such as, for example, the 7700 from ABI. The averages of the duplicates and the standard deviation were determined from the ct values determined. The result is depicted in Table 2.

TABLE 2

| Fraction | Average ct | Standard deviation |
| --- | --- | --- |
| Pellet | 24.7 | 0.26 |
| Supernatant | 28.1 | 0.25 |

The results demonstrate that the RNA isolated by the method of the invention, in particular from the pellet fraction, was well suited to amplification analyses. They furthermore confirm that the majority of the RNA was located in the pellet fraction, while only a much smaller proportion was detectable in the supernatant.

In summary, both the yield measurements and the further analyses of proteins and nucleic acids confirm that, when using the method of the invention, the biomolecules are clearly fractionated prior to downstream purification. The proteins are absolutely predominantly in the supernatant, while the nucleic acids are located in the pellet fraction.

The invention claimed is:

1. A method of isolating or detecting different kinds of biomolecules from a biological starting material fixed by crosslinking, comprising
   a) dissolving said crosslinkings of the starting material in a solution that comprises a detergent, but no proteolytically active compound to obtain a dissolved material,
   b) separating the dissolved material of step a) into soluble fraction (A) and insoluble fraction (B), wherein more than 50% of protein removable from the starting material is in soluble fraction (A), while more than 50% of nucleic acids removable from the starting material is in insoluble fraction (B), and
   c) isolating or detecting proteins from said soluble fraction (A) of step b), and isolating or detecting nucleic acids from said insoluble fraction (B) of step b).

2. The method according to claim 1, wherein the crosslinking of the starting material is dissolved in step a) by the following steps:
   (i) transferring the material to the solution,
   (ii) incubating said material in said solution at a temperature sufficient for liberating the soluble proteins, and
   (iii) subsequently further incubating said material at a temperature above 60° C.

3. The method according to claim 2, wherein in step (ii), the material is boiled in the solution.

4. The method according to claim 1, wherein step c) comprises isolating proteins from fraction (A) with the aid of customary methods of protein purification or protein isolation, and isolating nucleic acids from fraction (B) comprises disrupting the undissolved sample components and optionally further dissolving still-remaining crosslinkings in the starting material.

5. The method according to claim 4, wherein isolating the proteins takes place by chromatographic methods, electrophoretic separation, specific binding to protein-binding materials, protein capturing with the aid of specific antibodies, or by precipitation, and wherein isolating the nucleic acids proceeds by precipitation, binding to nucleic acid-binding materials, electrophoresis or chromatography.

6. The method according to claim 1, wherein detecting the proteins takes place by immunological methods, chromatographic methods, sequencing or electrophoresis, and detecting the nucleic acids takes place by PCR, electrophoresis, hybridization, or sequencing.

7. The method of claim 1, wherein the starting material is a formalin-fixed, paraffin-embedded (FFPE) biological material.

* * * * *

UNITED STATES PATENT AND TRADEMARK OFFICE
CERTIFICATE OF CORRECTION

| | | |
|---|---|---|
| PATENT NO. | : 10,011,826 B2 | Page 1 of 1 |
| APPLICATION NO. | : 13/132588 | |
| DATED | : July 3, 2018 | |
| INVENTOR(S) | : Holländer et al. | |

It is certified that error appears in the above-identified patent and that said Letters Patent is hereby corrected as shown below:

On the Title Page

Item (56) References Cited:
Under Foreign Patent Documents, Line 11, "WO 2007/068794 A1 6/2007" should read, --WO 2007/068764 A1 6/2007--.

Signed and Sealed this
Thirtieth Day of July, 2019

Andrei Iancu
*Director of the United States Patent and Trademark Office*